United States Patent
Charles

(10) Patent No.: US 11,166,708 B2
(45) Date of Patent: Nov. 9, 2021

(54) TRANS-SCLERAL ILLUMINATION SYSTEM FOR VITREORETINAL SURGERY

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/114,659

(22) Filed: Dec. 8, 2020

(65) Prior Publication Data

US 2021/0177393 A1    Jun. 17, 2021

Related U.S. Application Data

(60) Provisional application No. 62/947,736, filed on Dec. 13, 2019.

(51) Int. Cl.
    *A61B 17/02*     (2006.01)
    *A61B 3/00*      (2006.01)
    *A61B 90/30*     (2016.01)

(52) U.S. Cl.
    CPC ........ *A61B 17/0231* (2013.01); *A61B 3/0008* (2013.01); *A61B 90/30* (2016.02); *A61B 2090/306* (2016.02)

(58) Field of Classification Search
    CPC ... A61B 17/0231; A61B 90/30; A61B 3/0008; A61B 2090/306
    USPC ...................................................... 600/236
    See application file for complete search history.

(56) References Cited

U.S. PATENT DOCUMENTS

| | | | |
|---|---|---|---|
| 3,680,546 A * | 8/1972 | Asrican | A61B 3/0008 600/219 |
| 3,807,393 A * | 4/1974 | McDonald | A61B 1/07 600/208 |
| 3,944,341 A | 3/1976 | Pomerantzeff | |
| 4,213,678 A | 7/1980 | Pomerantzeff et al. | |
| 4,357,088 A | 11/1982 | Pomerantzeff | |
| 5,054,906 A * | 10/1991 | Lyons, Jr. | A61B 17/0231 351/205 |
| 5,695,492 A * | 12/1997 | Brown | A61B 90/20 606/4 |
| 9,044,304 B2 | 6/2015 | Raksi et al. | |
| 9,089,401 B2 | 7/2015 | Raksi et al. | |
| 9,877,648 B2 | 1/2018 | Farley et al. | |
| 9,895,264 B2 | 2/2018 | John et al. | |
| 10,172,516 B2 | 1/2019 | Charles | |
| 10,238,285 B2 | 3/2019 | Farley et al. | |
| 10,285,588 B2 | 5/2019 | Smith et al. | |
| 10,660,629 B2 * | 5/2020 | Brown | A61B 17/0206 |

(Continued)

OTHER PUBLICATIONS http://www.preceyes.nl/preceyes-surgical-system/, accessed Oct. 24, 2019 (8 pages).

*Primary Examiner* — Eduardo C Robert
*Assistant Examiner* — David C Comstock

(57) ABSTRACT

In one embodiment, an illumination system includes a speculum having two arms coupled to blades at distal ends thereof and a biasing member at proximal ends thereof. One or more optical fibers are disposed through at least one of the arms and have one or more termination points located within at least one of the blades. The optical fibers are configured to deliver light to an interior space of an eye when the eye is coupled to the speculum. In some embodiments, the illumination system further includes a temple support pad.

10 Claims, 8 Drawing Sheets

(56) References Cited

U.S. PATENT DOCUMENTS

2009/0171364 A1\* 7/2009 Olsen ................ A61B 17/0231
  606/107
2017/0105620 A1   4/2017 Charles \* cited by examiner

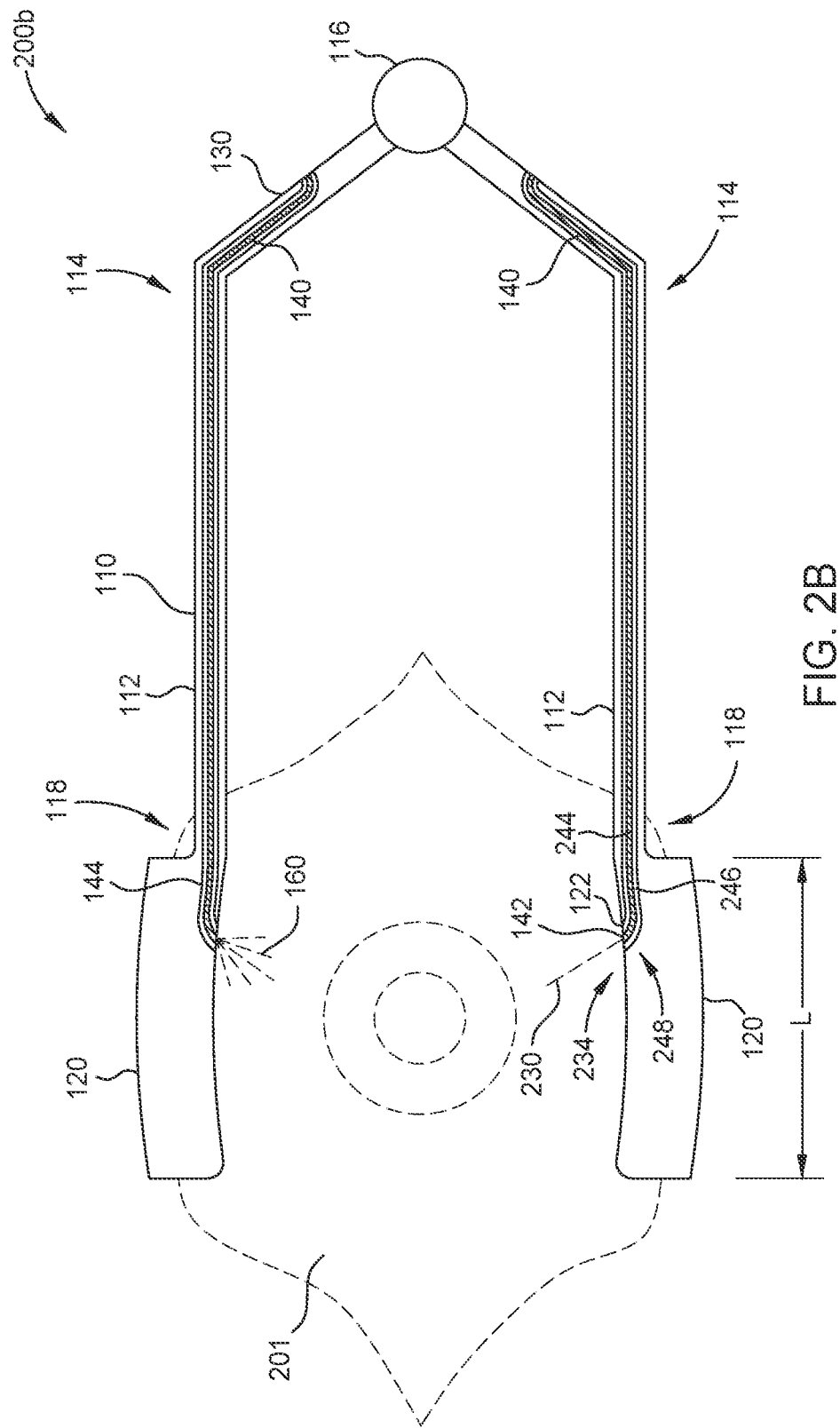

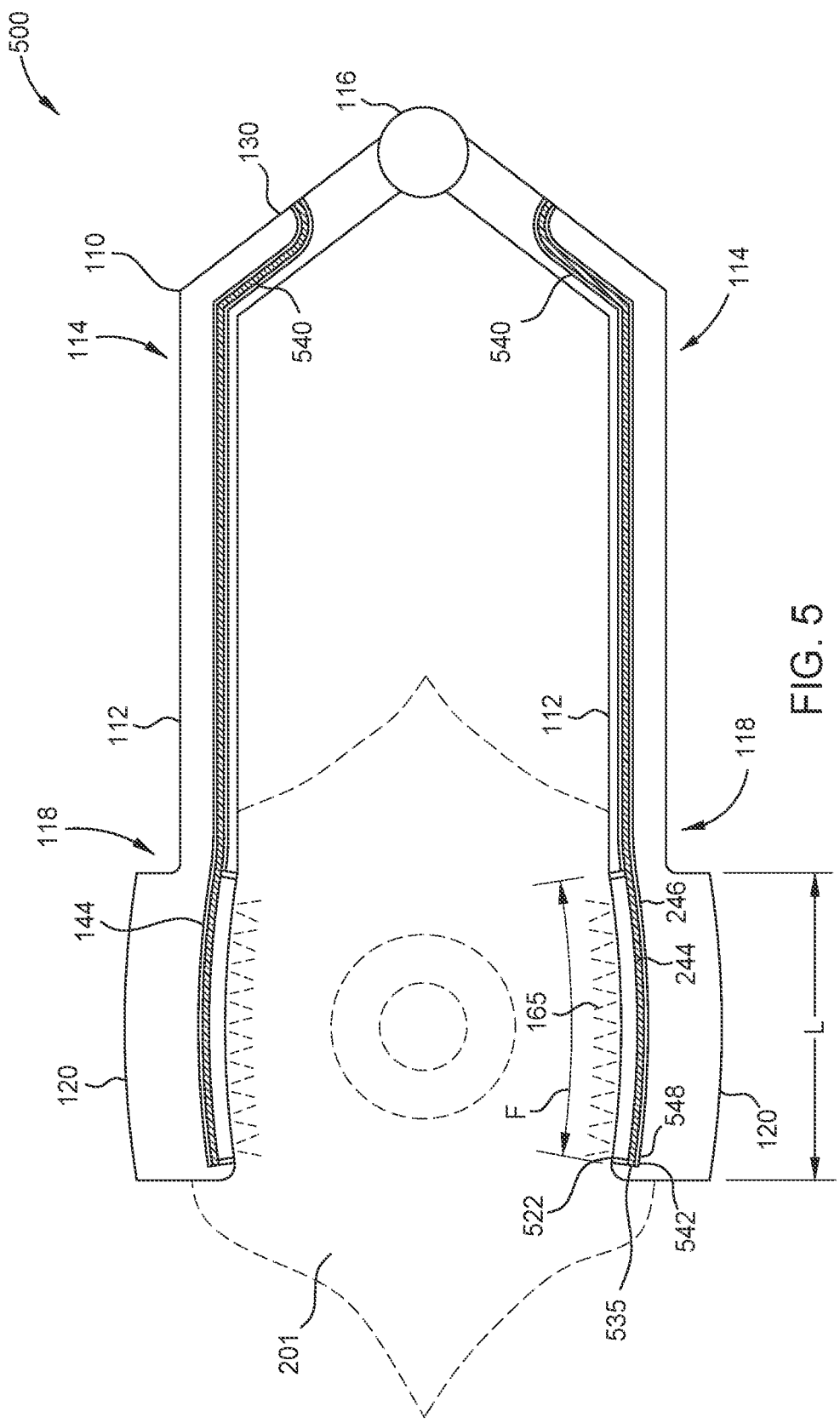

TRANS-SCLERAL ILLUMINATION SYSTEM FOR VITREORETINAL SURGERY

PRIORITY CLAIM

This application claims the benefit of priority of U.S. Provisional Patent Application Ser. No. 62/947,736 titled "TRANS-SCLERAL ILLUMINATION SYSTEM FOR VITREORETINAL SURGERY," filed on Dec. 13, 2019, whose inventor is Steven T. Charles, which is hereby incorporated by reference in its entirety as though fully and completely set forth herein.

BACKGROUND

Field

Embodiments of the present disclosure generally relate to instrumentation for surgical procedures, and more particularly, illumination systems for ophthalmic surgical procedures.

Description of the Related Art

Ophthalmic endoilluminators enable surgeons to illuminate the interior ocular space during surgical procedures, such as pars plana vitrectomies. Typically, ophthalmic endoilluminators include light-emitting distal tips attached to optical fibers. The distal tips of ophthalmic endoilluminators require introduction into the ocular space through incisions in the pars plana. By placing the distal tips of the ophthalmic endoilluminators into the ocular space and maneuvering the distal tips therein, light emitted from the tips may illuminate desired portions of the eye during the surgical procedure. A user (e.g., an ophthalmic surgeon or clinician) may illuminate the ocular space with the endoilluminators while using an analog or digital operating microscope to observe the eye during performance of surgical maneuvers.

One disadvantage exhibited by conventional ophthalmic endoilluminators is glare. Glare results when light from the endoilluminator is scattered and reflected such that the light interferes with the user's view. Glare is an unwanted stray light that provides no useful illumination, and either distracts the user or obscures an object under observation. For example, intraocular lenses, cataracts, corneal edema and opacities, cloudy vitreous, and the like, can scatter light produced by conventional ophthalmic endoilluminators.

Furthermore, conventional ophthalmic endoilluminators provide a non-uniform and relatively narrow light distribution within the intraocular space due to their light-emitting distal tips being disposed within the intraocular space, thus reducing beam spread therein. This relatively narrow light distribution leads to suboptimal visualization of the peripheral regions of the intraocular space, a common area for ocular defects such as retinal holes and tears. Accordingly, during surgical procedures, users may regularly adjust the position and/or orientation of conventional ophthalmic endoilluminators in order to adequately illuminate the peripheral regions of the eye.

Users may also frequently adjust the position and/or orientation of conventional ophthalmic endoilluminators in order to address possible crowding within the intraocular space, as multiple surgical devices and/or tools may be disposed within the intraocular space in addition to the endoilluminator itself. Thus, a user may have to adjust an endoilluminator in order to manipulate a separate surgical device and/or tool within the eye. In certain cases, these adjustments by the user to address the issues of poor peripheral illumination and crowding may result in the endoilluminator shaft striking ocular tissues such as the patient's lens or intraocular lens, thereby causing damage to the patient's eye and leading to the formation of defects (e.g. cataracts) or dislocation of the human or intraocular lens.

Accordingly, what is needed in the art are improved methods and apparatus for illumination of the ocular space during ophthalmic surgical procedures.

SUMMARY

The present disclosure generally relates to illumination systems for surgical procedures, and more particularly, non-invasive trans-scleral illumination systems for ophthalmic surgical procedures.

In one embodiment, a surgical illumination system is provided. The surgical illumination system includes a speculum for retracting eyelids of a patient. The speculum includes a first arm having a first proximal end and a first distal end and a second arm having a second proximal end and a second distal end, wherein the arms are movable about a pivot axis. A first blade is coupled to the first distal end and a second blade is coupled to the second distal end. The surgical illumination system further includes an optical fiber coupled to at least one of the first blade and the second blade to propagate light provided by a light source for illuminating at least a portion of an eye.

The following description and the related drawings set forth in detail certain illustrative features of one or more embodiments.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 2B illustrates a schematic top view of an exemplary speculum-supported illumination system fitted to an eye of a patient, according to an embodiment of the present disclosure.

FIG. 5 illustrates a schematic top view of another exemplary speculum-support illumination system fitted to an eye, according to an embodiment of the present disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to illumination systems for surgical procedures, and more particularly, non-invasive trans-scleral illumination systems for ophthalmic surgical procedures. In one embodiment, an illumination system includes a speculum having two arms coupled to blades at distal ends thereof and a biasing member at proximal ends thereof. One or more optical fibers are disposed through at least one of the arms and have one or more termination points located within at least one of the blades. The optical fibers are configured to deliver light to an interior space of an eye when the speculum is coupled to the eye. In some embodiments, the illumination system further includes an adjustable temple support pad.

As used herein, the term "proximal" refers to a location with respect to a device or a portion of the device that, during normal use, is closest to the user using the device and farthest from the patient in connection with whom the device is used. Conversely, the term "distal" refers to a location with respect to the device or the portion of the device that, during normal use, is farthest from the user using the device and closest to the patient in connection with whom the device is used. For example, the terms "distal" and "proximal" as used herein may refer to a relative location with respect to an illumination system, optic fiber, microscope, or a portion thereof.

Figure 1A:
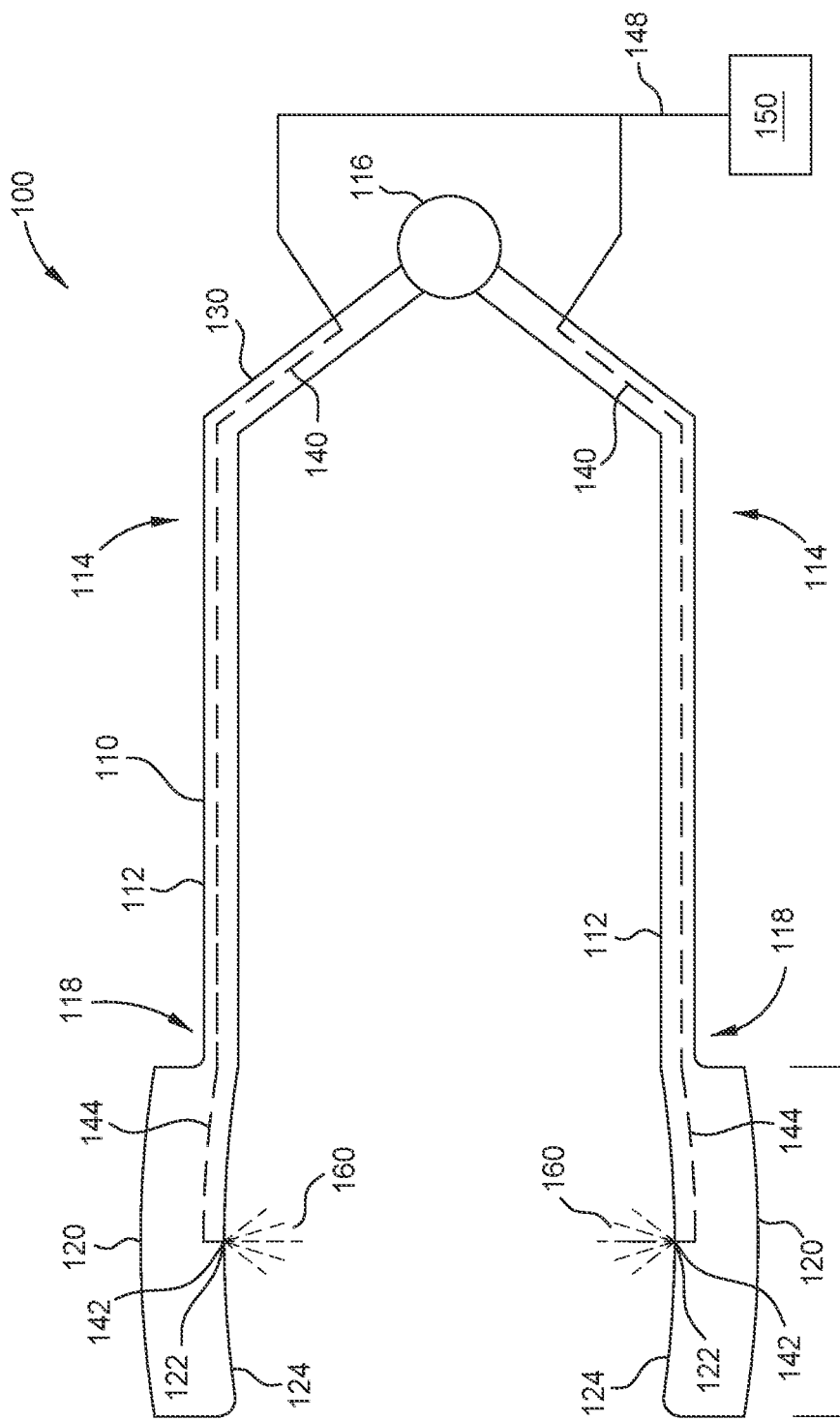
FIG. 1A illustrates a schematic view of an exemplary speculum-supported illumination system, according to an embodiment of the present disclosure.

FIG. 1A illustrates a schematic view of a speculum-supported illumination system 100. The speculum-supported illumination system 100 may be utilized to hold a patient's eyelids open and illuminate an interior ocular space of the patient's eye, for example, through the pars plana. For example, the speculum-supported illumination system 100 may be utilized to enable access to the patient's eye for a user and illuminate the ocular space therein for ophthalmic procedures including vitreoretinal surgeries and other procedures. Utilization of a speculum to support the illumination system 100 eliminates the need for the user to hold the illumination system 100 during surgical procedures as is necessary when using a conventional ophthalmic endoilluminator, and thus, affords the user a free hand to operate other surgical devices, tools, and the like.

The components of the speculum-supported illumination system 100 are generally formed of a material suitable for surgical procedures, such as vitreoretinal surgeries that involve removal of the vitreous of the eye, or other surgical procedures. For example, the components of the speculum-supported illumination system 100 may be formed of metals, plastics, or polymers. In one embodiment, the components of the speculum-supported illumination system 100 are formed of aluminum, stainless steel, titanium, or similar material.

The speculum-supported illumination system 100 includes a speculum 110 having two arms 112 coupled to one another by a biasing member 130 disposed at proximal ends 114 of the arms 112. The biasing member 130 may include any suitable biasing mechanism to bias the arms 112 in a separated and relaxed position (e.g., away from each other) about a pivot axis 116. In some examples, the biasing member 130 is an integral extension of each arm 112 and thus, the arms 112 and the biasing member 130 are an integrally formed (e.g., single, indistinguishable) structure. As depicted in FIG. 1A, the biasing member 130 may include or refer to the obtusely-angled extensions of each arm 112 that converge at the pivot axis 116. Accordingly, the biasing mechanism of the biasing member 130 may be overcome by squeezing the arms 112 together with a force greater than the biasing force of the biasing member 130 in the separated and relaxed position. In other examples, the biasing member 130 includes one or more distinct structures separate from the arms 112 (e.g., a coil spring, screw, and/or housing) which may be detachable therefrom. Generally, the arms 112 are parallel to one another when in a fully separated and relaxed position, as depicted in FIG. 1.

Each arm 112 is further coupled to a blade 120 near a distal end 118 of each arm 112. Although depicted at the distal ends 118, the blades 120 may be disposed at any suitable location along the arms 112 to preferentially retract desired portions of the patient's eyelids. The blades 120 are shaped to fit at least partially under the patient's eyelids and each include a contact surface 124 (shown in FIG. 1B) configured to press against the sclera of the patient's eyeball during use of the speculum-supported illumination system 100. Accordingly, the contact surface 124 has an outward curvature along a length L of each blade 120 to conform to a natural contour of the patient's eyeball and enable a substantial portion of the blades 120 to contact the sclera during use of the speculum-supported illumination system 100.

The speculum-supported illumination system 100 further includes one or more optical fibers 140 coupled to the blades 120 and configured to direct light beams 160 into an interior space of the patient's eye non-invasively through the sclera (see, for example, FIGS. 2B, 3, 4, and 5), and more specifically, through the pars plana. The pars plana is typically located about 3-5 millimeters (mm) radially outward of the cornea. Directing light through the pars plana of the patient's eye, in the manner described herein, provides several advantages over other locations of the sclera or the lens. For example, because the pars plana has a relatively low level of pigmentation compared to other tissues of the eye disposed more radially outward therefrom, the pars plana has a relatively high level of optical transmission, enabling more intense and diffuse illumination of the intraocular space compared with other tissues. Directing light through the pars plana and behind the intraocular lens also results in diminished glare, as the intraocular lens can refract distracting light toward a user. Such is a common occurrence with conventional ophthalmic endoilluminators, as light emitted by such endoilluminators may reflect off the retina and towards the intraocular lens. Transmitting light from an exterior location of the eye also facilitates improved illumination of the peripheral regions of the intraocular space, since disposition of the light source (e.g. speculum-supported illumination system 100) exterior to the ocular space enables a wider distribution of light therein. Still further, using the speculum-supported illumination system 100 eliminates the potential for intraocular tissue damage to the eye, such as lens damage, which may occur with the utilization of conventional intraocular endoilluminators due to the endoilluminator shafts striking ocular tissues during use thereof.

Each of the optical fibers 140 has one or more termination points 142 (e.g., light output locations) at a distal end 144 thereof and disposed at one or more locations along a length L of a respective blade 120. In one embodiment, the optical fibers 140 are coupled to external surfaces of the blades 120 and/or the arms 112. In one embodiment, the optical fibers 140 are housed within (e.g., disposed through internal cavities of; disposed along an internal surface of) the blades 120 and/or the arms 112 and have termination points 142 exposed through one or more openings 122 machined in the blades 120 and/or the arms 112. For example, the optical fibers 140 may pass through one or more openings near the proximal ends 114 of the arms 112 and into the arms 112 and blades 120.

The optical fibers 140 may be optically connected to a light source 150 at a proximal end 148 thereof for producing light that may be used to illuminate the interior space of the patient's eye during various intra-optical procedures. Light produced by the light source 150 is transmitted to the interior space of the patient's eye through the optical fibers 140. The light source 150 may generate a light at a particular luminous flux and chromaticity. Furthermore, the light may be emitted over a relatively wide or narrow range of wavelengths depending on the type of light source 150 employed. The light source 150 may employ various light producing technologies, including but not limited to, lamp-based light producing technologies, such as halogen and tungsten lamps and high-pressure arc lamps (metal-halides and Xenon (Xe)). Light emitting diodes (LEDs), superluminescent light emitting diodes (SLEDS), or lasers may also be employed as light-producing technologies.

In various embodiments, the speculum-supported illumination system 100 is implemented with fewer or more components than illustrated in the embodiment depicted in FIG. 1A. For example, the speculum-supported illumination system may include one or more additional linkages and/or bodies for utilization with other instruments for ophthalmic procedures, such as a contact lens mounting ring. An example of a speculum-supported illumination system with additional components will further be described with reference to FIG. 1B.

Figure 1B:
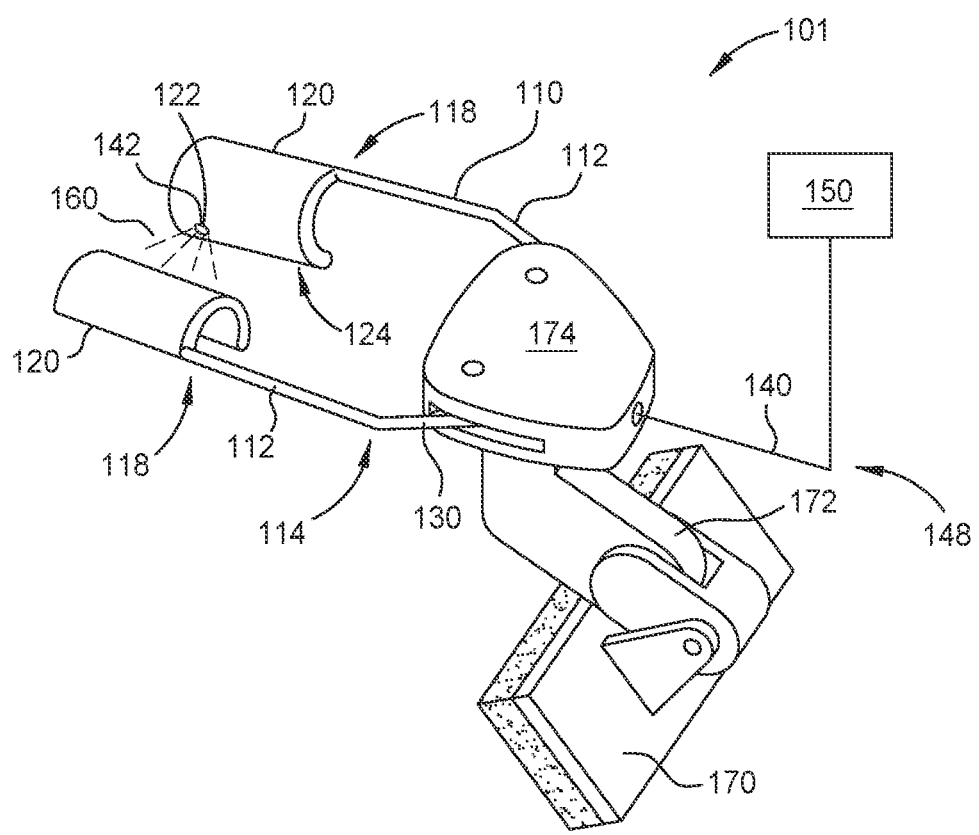
FIG. 1B illustrates a perspective view of an exemplary speculum-supported illumination system, according to an embodiment of the present disclosure.

FIG. 1B illustrates a perspective view of a speculum-supported illumination system 101. The speculum-supported illumination system 101 includes all of the components of speculum-supported illumination system 100, and further includes an optional temple support pad 170, a spherical joint 172, and a main body 174. The temple support pad 170 provides additional support to the speculum 110 to remain upright and in position while the speculum 110 rests on an eye of a patient. Because the temple support pad 170 is adjustable using the spherical joint 172, the temple support pad 170 may prevent various undesired motions of the speculum 110 as a third supporting base point, in addition to each of the blades 120. In this manner, the temple support pad 170 may provide stability. In some embodiments, the temple support pad 170 is configured to rest on a patient's temple during use of the speculum-supported illumination system 101. In other embodiments, the temple support pad 170 may be configured to rest on a patient's cheek, forehead, and/or other parts of the patient's face.

The spherical joint 172 may act as a universal joint to enable flexible positioning of the temple support pad 170 with respect to the patient. Further, the spherical joint 172 may be compressed with a force sufficient to maintain a fixed position. In some embodiments, the compressive force at the spherical joint 172 is mechanically adjustable, such as with a threaded compressive element. In some embodiments, the compressive supporting force at the spherical joint 172 is augmented by a preload force, such as may be provided by aspiring or other flexible biasing element.

The main body 174 provides an attachment point between the spherical joint 172 and the speculum 110. In some embodiments, the main body 174 may further act as an attachment point for one or more additional linkages and/or bodies. As illustrated in FIG. 1B, the main body 174 partially encases and supports the biasing member 130 therein, with the arms 112 of the speculum 110 extending from one or more openings thereof. Although the speculum-supported illumination system 101 is shown in FIG. 1B with blades 120 having solid (i.e., closed) bodies, any kind of speculum blades configured to encase or attach the optical fibers 140 may be fitted to the speculum 110 in place of, or in addition to, the blades 120. For example, the blades 120 may be wire (i.e., open body) blades. Generally, the blades 120 have a curved morphology to provide a pocket for accommodating and retaining the patient's eyelids during retraction thereof. It is further noted that the main body 174 may rest on the patient while the speculum 110 is used during ophthalmic procedures.

Figure 2A:
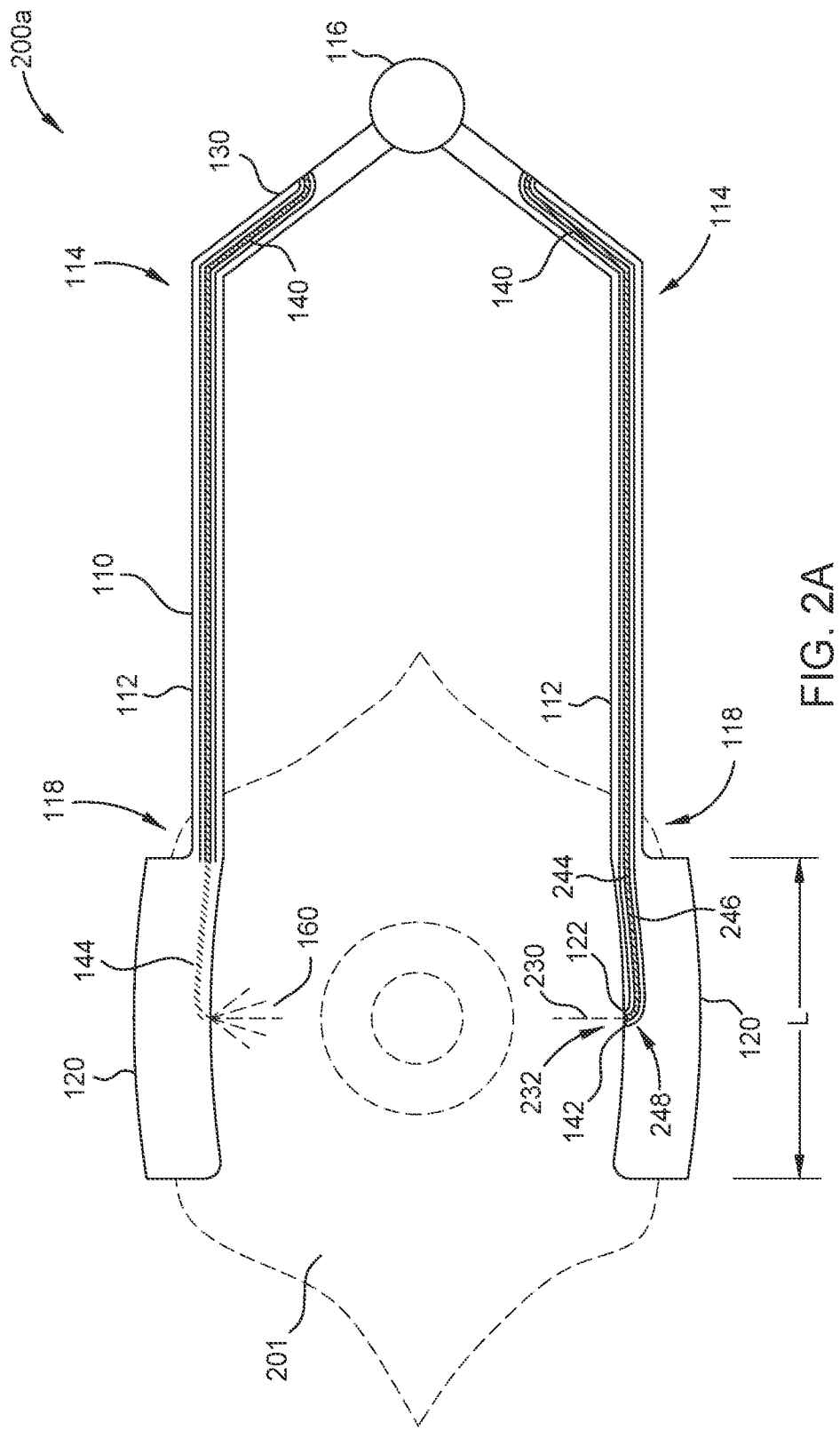
FIG. 2A illustrates a schematic top view of an exemplary speculum-supported illumination system fitted to an eye of a patient, according to an embodiment of the present disclosure.
Figure 2C:
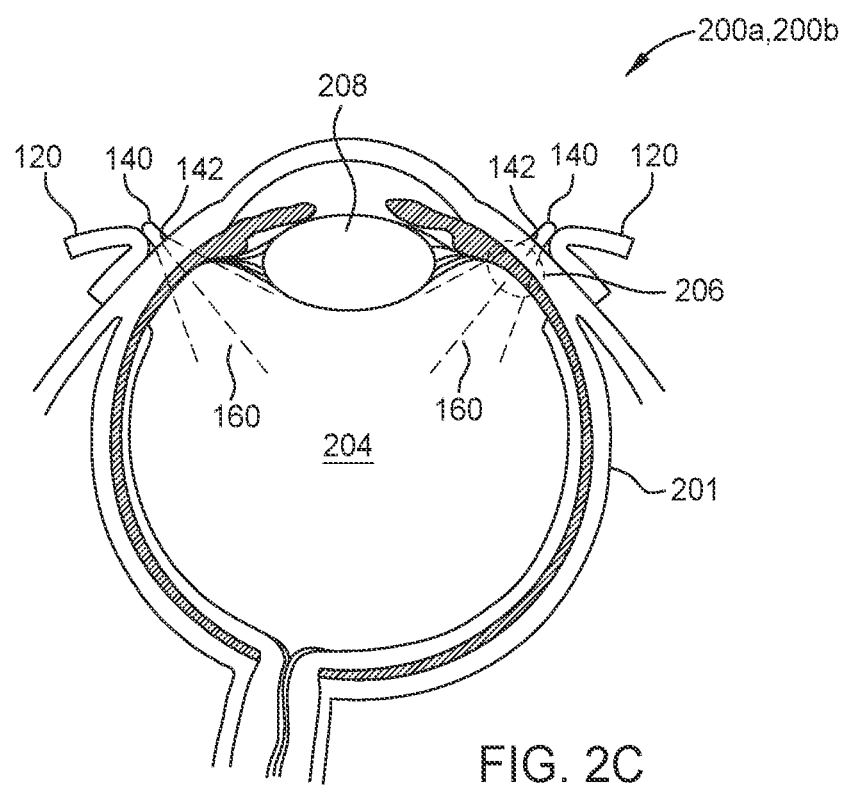
FIG. 2C illustrates a schematic side view of an exemplary speculum-supported illumination system illuminating an interior region of an eye, according to an embodiment of the present disclosure.
Figure 2D:
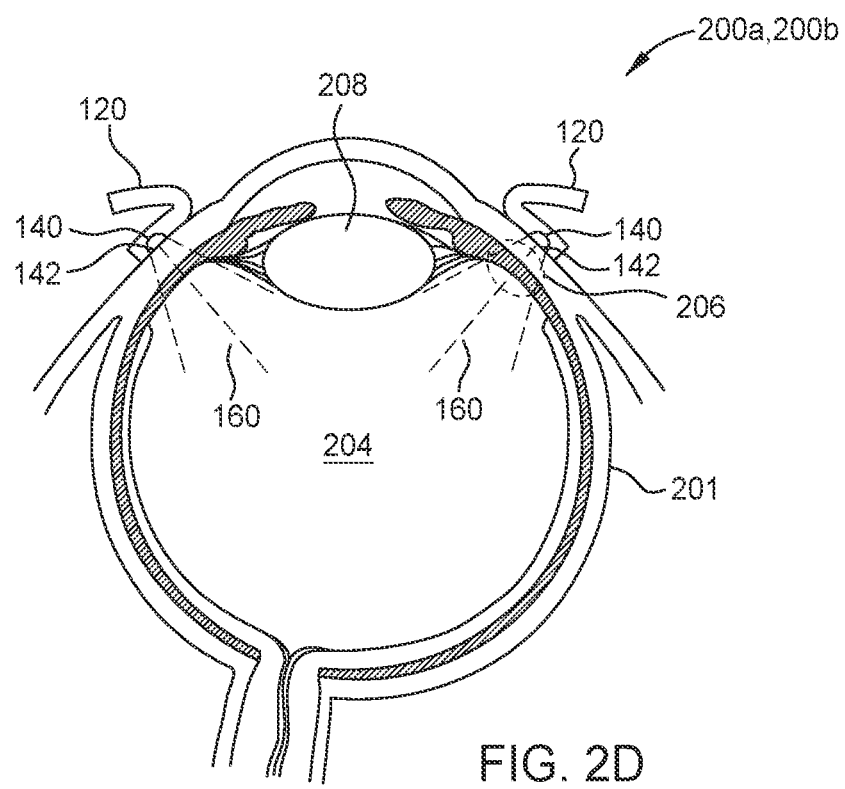
FIG. 2D illustrates a schematic side view of an exemplary speculum-supported illumination system illuminating an interior region of an eye, according to an embodiment of the present disclosure.

FIGS. 2A and 2B illustrate schematic top views of speculum-supported illumination systems 200a, 200b when resting on an eye 201 of a patient, according to some embodiments. The top views of FIGS. 2A and 2B correspond to a partial perspective of an ophthalmic surgeon performing a surgical procedure, such as a vitreoretinal surgery, and looking down into the eye 201 having eyelids held open (i.e. retracted) by the two blades 120 of the speculum 110. FIGS. 2C and 2D illustrate schematic side views of the speculum-supported illumination systems 200a, 200b when resting on the eye 201 of the patient according to some embodiments. Accordingly, FIGS. 2A, 2B, 2C, and 2D are herein described together for clarity.

The optical fibers 140 may have any of a variety of configurations. As an example, in FIG. 2A, each of the optical fibers 140 has an optically transmissive core 244 that is also surrounded by one or more claddings 246. In another example, each optical fiber 140 may include an optical fiber array (e.g., a plurality of optical fibers in a regular linear arrangement, a 2-dimensional pattern arrangement, or some other arrangement) and/or a multi-core optical fiber (e.g., a multi-mode (MM) fiber with multiple optic cores 244). The optical fibers 140 may include one or more of a polarization maintaining fiber, a polarizing fiber, and/or any other fiber suitable for transmission of light. Thus, the optical fibers 140 may induce polarization of unpolarized light propagated therethrough, maintain an existing polarization direction of light propagated therethrough, and/or change a direction of already polarized light being propagated therethrough.

The termination point 142 of each optical fiber 140 may be disposed at any desired location along a length L of the blade 120. A light beam 160 is emitted from the termination point 142 of each optical fiber 140 and transmitted through the sclera (e.g., pars plana) of the eye 201 into an interior space 204 (shown in FIGS. 2C and 2D) thereof. Note that a light beam 160 is shown only in relation to one of the optical fibers 140 for simplicity. Generally, the location of the termination point 142 is selected depending on a desired distribution of the light beam 160 within the interior space 204. In FIG. 2A, the single termination point 142 of each optical fiber 140 includes a distal tip 248 having a normal end face 232 arranged at an angle normal to an optical axis 230 of the optical fiber 140. Thus, to enable the normal end faces 232 to sit substantially flush with an outer or inner surface of the blades 120 or against the sclera of the eye 201 during use thereof, the optical fibers 140 are bowed (e.g., curved or bent) at each blade 120. In some examples, the optical fibers 140 are bowed at an angle less than 90°. In some examples, the optical fibers 140 are bowed at an angle of about 90°. In other examples, the optical fibers 140 are bowed at an angle greater than 90°. Note that details such as the distal tip 248, normal end face 232, and optical axis 230 are shown only in relation to one of the optical fibers 140 for simplicity.

In certain applications, it is generally desirable for the light beam 160 emitted from the termination point 142 to have a relatively wide angular distribution to enable illumination of a corresponding surgical field within the eye 201. Therefore, as depicted in FIG. 2B with speculum-supported illumination system 200b, the termination point 142 of each optical fiber 140 may include the distal tip 248 having a tapered end face 234 arranged at an oblique angle (e.g., angled, inclined) relative to the optical axis 230. Utilizing tapered end faces 234 provides wider angular distributions as compared to the normal end faces 232, which may advantageously produce wider light beams 160 selectively directed in a desired direction from the optical fibers 140. The angular distribution of the light beams 160 is at least partially dependent on the orientation and length of the tapered end faces 234, and thus, having longer tapered end faces 234 may produce wider angular distributions of the light beams 160. Similar to the embodiment in FIG. 2A, the optical fibers 140 in FIG. 2B are bowed at the blades 120 to enable the tapered end faces 234 to sit flush with the outer or inner surface of the blades 120 or against the sclera of the eye 201 adjacent the pars plana. Generally, a bowing angle of less than 90° is sufficient to enable the tapered end faces 234 to sit flush with the outer or inner surface of the blades 120 or against the sclera of the eye 201.

As illustrated in FIGS. 2C and 2D, each of the speculum-supported illumination systems 200a, 200b include optical fibers 140 disposed along an outer surface of each arm 112 and blade 120 (see, for example, FIG. 2C) or disposed through inner cavities thereof (see, for example, FIG. 2D) and terminating at a single termination point 142 located at each blade 120. In examples where the optical fibers 140 are disposed through an inner cavity of each arm 112 and blade 120, the termination points 142 may be exposed to an exterior environment through an adjacent opening 122 in the blades 120. As depicted, the light beams 160 emitted by the optical fibers 140 are directed into the interior space 204 through the sclera of the eye 201 in a region 206 corresponding to the pars plana. By introducing the light beams 160 into the interior space 204 through the region 206, light scattering caused by extraocular or intraocular lenses, such as intraocular lens 208, may be significantly reduced or eliminated, thereby providing 360° of the interior space 204 and reduced glare during ophthalmic procedures.

Although illustrated in FIGS. 2A-2D as having termination points adjacent to and facing the openings 122 in the blades 120, in some embodiments the optical fibers 140 may have termination points 142 facing away from the openings 122. In such embodiments, a turning prism, mirror, or other suitable device may be utilized in combination with the optical fibers 140 to direct light emitted from the termination points 142 through the openings 122. Accordingly, the end faces of the termination points 142 of the optical fibers 140 may be disposed in any desired orientation within the blades 120.

Figure 3:
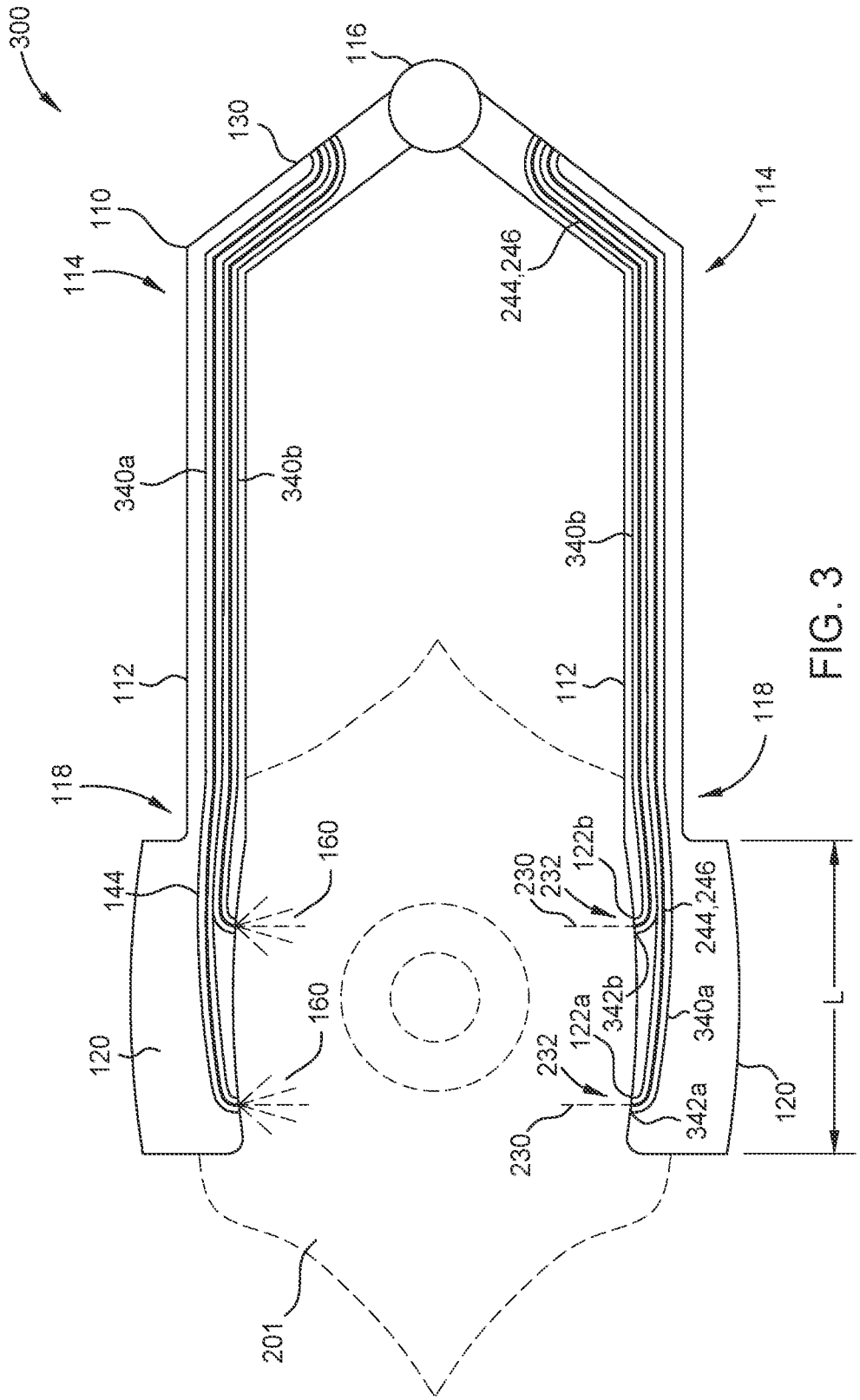
FIG. 3 illustrates a schematic top view of another exemplary speculum-support illumination system illuminating fitted to an eye, according to an embodiment of the present disclosure.

FIG. 3 illustrates a schematic top view of another speculum-supported illumination system 300 resting on an eye 201 of a patient, according to another embodiment. Unlike the speculum-supported illumination systems 200a, 200b, the speculum-supported illumination system 300 includes multiple optical fibers 340 disposed along or through each arm 112 and blade 120 of the speculum 110 and terminating at separate termination points 342 (two optical fibers 340a, 340b having termination points 342a, 342b, respectively, are depicted in each blade 120). Where the optical fibers 340 are disposed through internal cavities of the arms 112 and blades 120, each termination point 342 may be exposed to an exterior environment through an individual opening 122 in the blades 120 (two openings 122a, 122b are depicted in each blade 120).

Although depicted as having two optical fibers 340, the speculum-supported illumination system 300 may include more than two optical fibers 340, such as three optical fibers 340, four optical fibers 340, or five or more optical fibers 340, each having a separate termination point 342. The utilization of multiple optical fibers 340 provides a wider angular distribution of illumination, as light beams 160 from each optical fiber 340 may create a combined illuminating effect within the interior space 202. Therefore, the angular distribution of illumination is at least partially dependent on the number of optical fibers 340 utilized. Furthermore, as described above with reference to FIG. 2B, the angular distribution of illumination by the light beams 160 may further be modulated by tapering the end faces of distal tips 348. Thus, even though the optical fibers 340 of FIG. 3 are depicted having normal end faces 232 arranged at angles normal to the optical axes 230, the speculum-supported illumination system 300 may include optical fibers 340 having tapered end faces similar to the tapered faces 234 in some embodiments.

Figure 4:
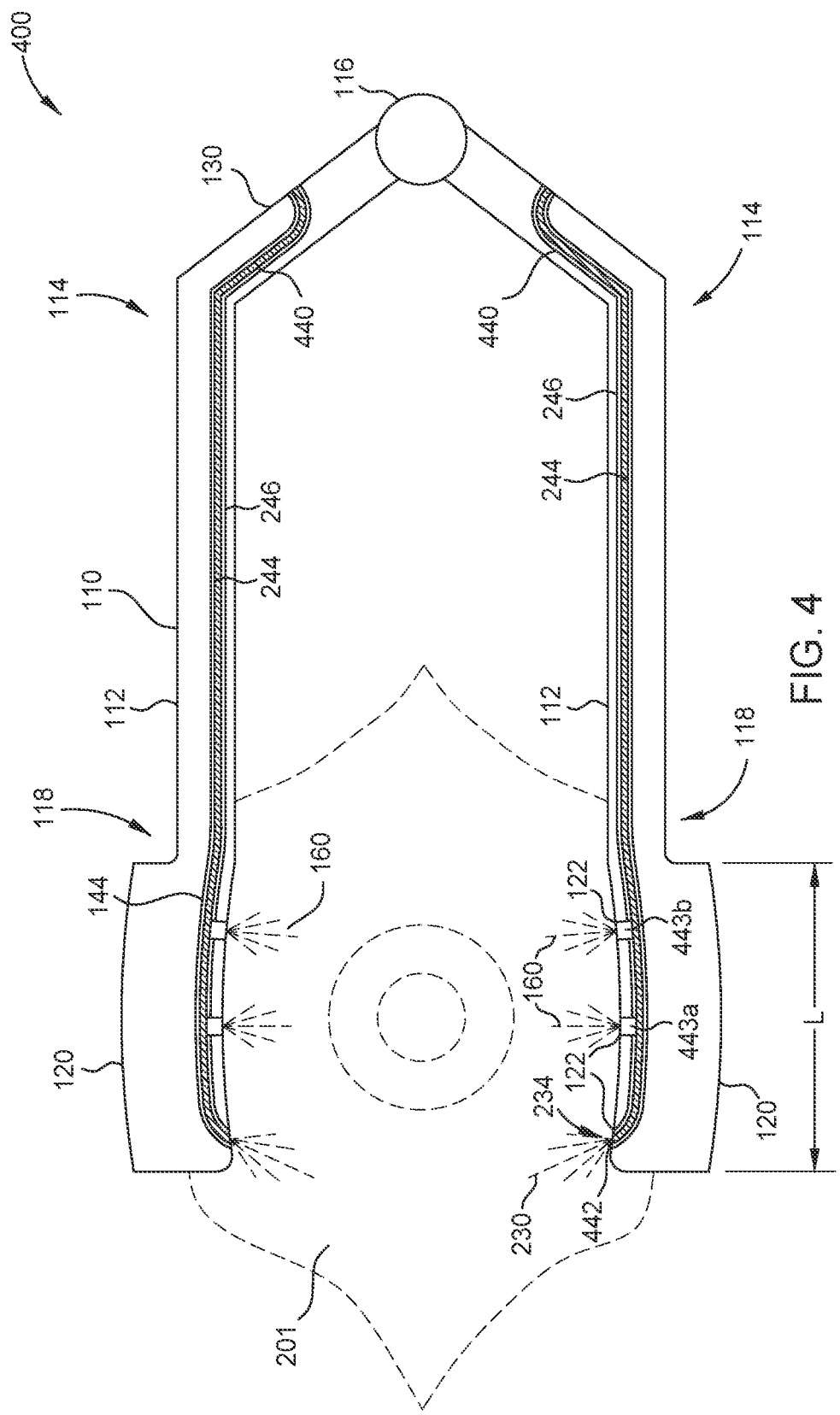
FIG. 4 illustrates a schematic top view of another exemplary speculum-support illumination system fitted to an eye, according to an embodiment of the present disclosure.

FIG. 4 illustrates a schematic top view of another speculum-supported illumination system 400 resting on an eye 201 of a patient, according to another embodiment. The embodiment of FIG. 4 is similar to those described with reference to FIGS. 2A, 2B, 2C and 2D, and includes a single optical fiber 440 disposed along or through each arm 112 and blade 120 of the speculum 110 and terminating at termination points 442. However, unlike the embodiments above, each optical fiber 440 in FIG. 4 is machined to have one or more light output points 443 (two output points 443a, 443b are shown in FIG. 4) through the cladding layer 246 of the optical fibers 440 along a length F thereof. For example, at output points 443, cladding layer 246 is stripped thereby exposing the core 244 of the optical fiber 440. In embodiments where the optical fibers 440 are disposed within the arms 112 and the blades 120, such as the embodiment shown in FIG. 4, the output points 443 are aligned with respective openings 122 in the blades 120, thereby allowing light that is emitted by the optical fibers 440 from the output points to reach the patient's eye 201 through openings 122.

The output points 443 enable a portion of the light being reflected through each core 244 to exit the optical fibers 440 therethrough and thus, each optical fiber 440 emits multiple light beams 160 rather than a single light beam 160 from the optical fiber 440's respective termination points 442. The one or more output points 443 may be formed in any suitable locations along the optical fibers 440 and, in embodiments where the optical fibers 440 are disposed within the blades 120, aligned with desired locations of the openings 122 along the length L of the blades 120. In some embodiments, the output points 443 may be additionally or alternatively formed along a length of the arms 112. In further embodiments, the termination points 442 of the optical fibers 440 may be light non-emitting (e.g., enclosed by the cladding layer 246). Accordingly, the optical fibers 440 may include termination points 442 having distal tips with end faces arranged at an angle normal to the length L and disposed within the blades 120. By having one or more output points 443 formed in the optical fibers 440, a single optical fiber 440 may function in a similar fashion to the embodiment described with reference to FIG. 3, wherein multiple optical fibers 140 are disposed along or through each blade 120 and emit a single light beam 160 from each of their termination points 142.

FIG. 5 illustrates a schematic top view of another speculum-supported illumination system 500 when resting on an eye 201 of a patient, according to another embodiment. As illustrated in FIG. 5A, the speculum-supported illumination system 500 includes a single optical fiber 540 disposed along or through each arm 112 of the speculum 110 and each blade 120. The optical fibers 540 are side-emitting optical fibers or edge-emitting fibers and may provide illumination 165 along an entire (e.g., uninterrupted) length F of the optical fiber 540. For example, optical fibers 540 may have cladding layers 246 stripped along desired sides of the optical fibers 540, thereby exposing the cores 244 of the optical fibers 440 and allowing light to be emitted along the stripped sides of the optical fibers 540. Thus, in embodiments where the optical fibers 540 are disposed within internal cavities of the arms 112 and blades 120, an outer surface (e.g., outer surface of the cladding layer 136) of the optical fibers 540 may be exposed through a longitudinal slit 522 along the length L of the blades 120 to allow light beams 160 emitted from the optical fibers 540 to be continuously output along the length L. In some examples, the slit 522 may also partially extend along a length of the arms 112 as well.

Because the optical fibers 540 are side-emitting or edge-emitting fibers, no bowing of the optical fibers 540 is necessitated to direct light beams 160 towards the eye 201. Furthermore, the optical fibers 540 may include a termination point 542 having a distal tip with an end face 535 arranged at an angle normal to the length L, and thus, the termination points 542 may be light non-emitting. Utilizing the side-emitting or edge-emitting fibers 540 may provide a wider angular distribution of emitted light as compared to the embodiments described above, which may advantageously produce more uniform illumination of the interior space 204 of the eye 201 and reduction of glare therein.

The extraocular speculum-supported illumination systems described herein provide novel, non-invasive ways to illuminate the intraocular space and reduce the occurrence of glare, which is a common problem with conventional ophthalmic endoilluminators and chandelier illuminators. By transmitting light through the pars plana region of the sclera and behind the human lens, light scattering caused by extraocular or intraocular lenses may be significantly reduced or eliminated, thus reducing glare for a user observing, for example, the peripheral retina of a patient's eye. Furthermore, the reduced pigmentation of the pars plana in relation to other regions of the sclera enables significantly high optical transmission of light therethrough, resulting in uniform, diffuse, and optimal illumination of the intraocular space when light is directed through the pars plana.

The utilization of an extraocular speculum-supported illumination system additionally provides users with greater flexibility during performance of ophthalmic procedures, as the user is afforded more room to operate in the intraocular space and is no longer limited by the need to hold the illumination system in place. Further, using an extraocular speculum-supported illumination system eliminates the potential for intraocular tissue damage to the eye, such as lens damage, which may occur with the utilization of conventional intraocular endoilluminators due to the endoilluminator shafts striking the ocular tissues during use thereof. For example, in certain cases, endoilluminator shafts may collide with the human lens when users adjust the endoilluminator in order to illuminate the peripheral retina. Therefore, the illumination systems described herein provide safer and more effective apparatuses and methods of ocular illumination for ophthalmic procedures.

While the foregoing is directed to embodiments of the present disclosure, other and further embodiments of the disclosure may be devised without departing from the basic scope thereof, and the scope thereof is determined by the claims that follow.

What is claimed is:

1. A surgical illumination system, comprising:
    a speculum for retracting eyelids of a patient, the speculum comprising:
        a first arm having a first proximal end and a first distal end, the first distal end coupled to a first blade; and
        a second arm having a second proximal end and a second distal end, the second distal end coupled to a second blade, the first and second arms movable about a pivot axis; and
        an optical fiber coupled to at least one of the first blade and the second blade, the optical fiber configured to propagate light provided by a light source for illuminating at least a portion of an eye;
    wherein the first and second blades are each shaped to fit under the patient's eyelids and each include a contact surface configured to press against a sclera of a patient's eyeball;
    wherein the contact surface has an outward curvature along a length of each blade to conform to a natural contour of the eyeball and enable a substantial portion of the blade to contact the sclera during use;
    wherein a distal end of the optical fiber is disposed within at least one of the first blade and the second blade, and a proximal end of the optical fiber is optically connected to the light source;
    wherein the optical fiber further comprises a termination point at the distal end;
    wherein the termination point of the optical fiber is exposed to an exterior environment of the first blade or the second blade via an opening in the first blade or the second blade configured to direct light beams into an interior space of the eye through the pars plana.

2. The surgical illumination system of claim 1, wherein the light source comprises an LED light source.

3. The surgical illumination system of claim 1, wherein the light source comprises a lamp-based light source.

4. The surgical illumination system of claim 1, wherein the light source comprises a laser light source.

5. The surgical illumination system of claim 1, wherein the termination point includes a distal tip having an end face arranged at an angle normal to an optical axis of the optical fiber.

6. The surgical illumination system of claim 1, wherein the termination point includes a distal tip having an end face arranged at an oblique angle relative to an optical axis of the optical fiber.

7. The surgical illumination system of claim 1, wherein the optical fiber further includes one or more light output points along a length of the optical fiber and aligned with one or more openings of the first blade or the second blade, the one or more light output points configured to propagate light toward the interior space of the eye.

8. The surgical illumination system of claim 1, wherein the optical fiber further comprises a light non-emitting termination point at the distal end.

9. The surgical illumination system of claim 8, wherein the optical fiber includes one or more light output points along a length of the optical fiber and aligned with one or more openings of the first blade or the second blade.

10. The surgical illumination system of claim 8, wherein the optical fiber is a side-emitting optical fiber configured to emit light along an uninterrupted portion of the optical fiber.

\* \* \* \* \*